United States Patent [19]

Becker

[11] Patent Number: 4,760,185

[45] Date of Patent: Jul. 26, 1988

[54] PROCESS FOR THE ORTHO-ALKYLATION OF OPTIONALLY ALKYL-SUBSTITUTED M-PHENYLENEDIAMINES

[75] Inventor: Hans-Joachim Becker, Leverkusen, Fed. Rep. of Germany

[73] Assignee: Bayer Aktiengesellschaft, Leverkusen, Fed. Rep. of Germany

[21] Appl. No.: 860,144

[22] Filed: May 6, 1986

Related U.S. Application Data

[63] Continuation of Ser. No. 694,575, Jan. 24, 1985, abandoned.

[30] Foreign Application Priority Data

Jan. 28, 1984 [DE] Fed. Rep. of Germany ....... 3402983

[51] Int. Cl.$^4$ ............................................. C07C 85/24
[52] U.S. Cl. ..................................... 564/409; 564/315
[58] Field of Search ................................ 564/409, 315

[56] References Cited

FOREIGN PATENT DOCUMENTS 560990 7/1958 Canada ................................ 564/409
620573 5/1961 Canada ................................ 564/409
385794 4/1973 Spain .

*Primary Examiner*—Glennon H. Hollrah
*Assistant Examiner*—John A. Sopp
*Attorney, Agent, or Firm*—Sprung Horn Kramer & Woods

[57] ABSTRACT m-Phenylenediamines are alkylated in the orthoposition by heating them with an Al/Zn alloy and aluminium chloride, and reacting them with lower alkenes at elevated pressures and temperatures when the evolution of hydrogen is complete.

13 Claims, No Drawings

PROCESS FOR THE ORTHO-ALKYLATION OF OPTIONALLY ALKYL-SUBSTITUTED M-PHENYLENEDIAMINES

This is a continuation of application Ser. No. 694,575, filed Jan. 24, 1985, now abandoned.

The invention relates to a process for the orthoalkylation of optionally alkyl-substituted m-phenylenediamines.

Processes for the preparation of aromatic amines which are alkylated in the ring by reacting aromatic amines with olefins in the presence of aluminum or alloys thereof, such as aluminum amalgam or an Al/Ni alloy, or in the presence of the aluminum anilides formed therefrom, at elevated temperatures (200°–350° C.) and under elevated pressure (100–200 atmospheres) have been known for a long time (for example German Patent Specification No. 951,501).

It is also known (German Auslegeschrift No. 1,048,277), to increase the yields of aromatic amines alkylated in the ring, while at the same time shortening the reaction time, by adding Friedel-Crafts catalysts, such as aluminum chloride, or bleaching earths additionally in the alkylation by the known process.

Furthermore, it is also known to add iodine or iodine compounds to the aluminum or compounds thereof in the ring-alkylation of aromatic amines in accordance with German Patent Specification No. 951,501 (see German Auslegeschrift No. 1,044,097).

The alkylation of m-phenylenediamine and of 2,4-toluylenediamine and 2,6-toluylenediamine with ethylene is described particularly in German Auslegeschrift No. 1,048,277 in Examples 26 to 31 and in Example 34. Thus in Examples 26 to 28, the said toluylenediamines are reacted with ethylene at 280° to 300° C. and under a pressure of 200 atmospheres in the presence of aluminum chloride and a solution of aluminum anilide in aniline. The reaction is carried out in the presence of aluminum, aluminum chloride, mercury chloride and aniline in accordance with Examples 29 and 30, and, in Example 31, the alkylation is carried out in the presence of aluminum, aluminum chloride and mercury chloride. In accordance with Example 34 m-phenylenediamine is reacted with ethylene in the presence of an aluminum anilide solution and anhydrous aluminum chloride.

In addition, the ortho-alkylation of the said m-phenylenediamines is also described in a summarizing paper (R. Stroh and collaborators, Angew. Chem. 69, 124–131 (1957)). Here too, only alkylation with the addition of Al anilide in aniline solution is recommended as a suitable method.

Disadvantages in the processes mentioned are the addition of an auxiliary amine in the form of aluminum anilide/aniline solution or aniline, as a result of which the space-time yield of the desired product is reduced considerably, the simultaneous ring-alkylation of the auxiliary amine, in which byproducts, such as 2-ethylaniline, are formed to a considerable extent, and the indispensable removal of the residual aniline and the byproducts, which requires a considerable outlay on distillation (cf. Examples 26 to 30 and 34 of German Auslegeschrift No. 1,048,277). The addition of mercury chloride is also a disadvantage for ecological reasons.

A process has now been found for the ortho-alkylation of an optionally alkyl-substituted m-phenylenediamine which is characterized in that the appropriate m-phenylenediamine is heated with an Al/Zn alloy and aluminum chloride, and are reacted with a lower alkene at elevated pressure and temperature when the evolution of hydrogen is complete.

In addition to m-phenylenediamine, optionally alkyl-substituted m-phenylenediamines which can be employed in the process according to the invention are m-phenylenediamines containing, as substituents, one or more alkyl, cycloalkyl or aralkyl groups having 1 to 8, preferably 1 to 3, atoms, such as 2,4-toluylenediamine, 2,6-toluylenediamine, 1-ethyl-2,4-phenylenediamine, 1-ethyl-2,6-phenylenediamine, 1-propyl-2,4-phenylenediamine, 1,3-dimethyl-4,6-phenylenediamine or 1-benzyl-2,4-phenylenediamine, preferably 2,4-toluylenediamine and 2,6-toluylenediamine. The phenylenediamines can be employed either on their own or as a mixture with one another.

Suitable Al/Zn alloys are those having a zinc content of about 2 to 30% by weight, preferably 5 to 20% by weight. The aluminum content is, correspondingly, about 70 to 98% by weight, preferably 80 to 95% by weight. The alloys can be employed in the form of turnings, granules, grit or powder.

The amount of Al/Zn alloy employed can be varied and depends, inter alia, on the proportion of Zn in the Al/Zn alloy. In general about 0.5 to 4% by weight, preferably 1 to 2% by weight, of Al/Zn alloy, relative to the m-phenylenediamine to be alkylated, are employed.

The amount of aluminum chloride employed is usually about 1 to 7% by weight, preferably 2.5 to 4% by weight, relative to the m-phenylenediamine to be alkylated.

In the process according to the invention, the optionally alkyl-substituted m-phenylenediamine to be ortho-alkylated is first heated with an Al/Zn alloy and the (anhydrous) aluminum chloride at temperatures of about 150° to 250° C., preferably 170° to 220° C., until no further evolution of hydrogen can be observed. The mixture is then reacted with the lower alkene in an autoclave at temperatures of about 250° to 330° C., preferably 280° to 310° C. The pressures in this reaction are about 50 to 250 bar, preferably 80 to 120 bar. When the absorption of the alkene is complete, the reaction mixture is allowed to react a little further and, after the pressure of the excess alkene has been released, is worked up.

Lower alkenes which can be employed in the process according to the invention are ethylene and propylene, preferably ethylene.

The reaction mixture is worked up in a known manner by adding water or aqueous sodium hydroxide solution to the reaction mixture, whereby the catalyst is decomposed. The organic phase can then be subjected to vacuum distillation.

The m-phenylenediamines can be ortho-alkylated in a yield of about 96 to 98% by the process according to the invention. As already mentioned, compared with a process in which aluminum anilide and aniline or similar low-boiling aromatic monoamines are added, in the process according to the invention the space-time yield is considerably increased and the outlay on distillation is substantially reduced. The economic efficiency of the ortho-alkylation is thereby substantially increased compared with the processes corresponding to the state of the art.

Since, according to Example 10 of German Patent Specification No. 951,501, a conversion of only approx. 25% was achieved in the reaction of aniline and ethylene when using an Al/Ni alloy, in spite of severe reaction conditions, negative results would also have been expected in the ortho-alkylation of optionally alkyl-substituted m-phenylenediamines using Ni/Al alloys. In fact, no appreciable evolution of hydrogen and no alkylation reaction at all are observed either in the reaction of toluylenediamine and ethylene in the presence of an Al/Ni alloy, and this is also the case when pure aluminum is employed (cf. Example 1). Equally poor results are observed in the ortho-alkylation of toluylenediamines using aluminum alloys containing, for example, magnesium, tin, lead, cadmium or iron. It is, therefore, particularly surprising that it is in fact an Al/Zn alloy which gives good results in the ortho-alkylation of optionally alkyl-substituted m-phenylenediamines.

All in all, it can be stated that the ortho-alkylation of optionally alkyl-substituted m-phenylenediamines by means of an Al/Zn alloy and aluminum chloride can be carried out by the process according to the invention in just as simple a manner as the alkylation of monoamines by means of aluminum and aluminum chloride.

The ortho-alkylated m-phenylenediamines are particularly suitable for use as crosslinking components for polyurethane plastics (see German Auslegeschrift No. 2,622,951).

The examples which follow are intended to illustrate the process according to the invention, but without limiting it to the examples.

EXAMPLE 1

250 g of toluylenediamine 65/35 (a mixture of 65% by weight of 2,4-toluylenediamine and 35% by weight of 2,6-toluylenediamine) are heated with 4.7 g of an Al/Zn alloy consisting of 70% by weight of Al and 30% by weight of Zn and 8.3 g of aluminum chloride (anhydrous) to 200° C. (not more than 220° C.), with stirring. The evolution of hydrogen begins at 150° C. and is complete after about 45 minutes.

The reaction batch is then reacted with ethylene in a stirred autoclave at temperatures of 290°–300° C. and under a pressure of 200 bar. The absorption of ethylene is complete after 25–30 minutes.

Working up with aqueous sodium hydroxide solution gives an alkylation product containing, according to analysis by gas chromatography, 98% of dialkylated toluylenediamines (1-methyl-3,5-diethyl-2,4-phenylenediamine and 1-methyl-3,5-diethyl-2,6-phenylenediamine).

If pure aluminum or an Al/Ni alloy is employed instead of the Al/Zn alloy, no appreciable evolution of hydrogen or alkylation takes place.

EXAMPLE 2

250 g of toluylenediamine 65/35 are reacted, as described in Example 1, with 4.7 g of an Al/Zn alloy (70% by weight of Al; 30% by weight of Zn) and 4.15 g of aluminum chloride.

The ethylation reaction analogous to Example 1 is complete after 45 minutes and gives an alkylation product having a 98.4% content of the diethyl compounds mentioned in Example 1.

EXAMPLE 3

250 g of toluylenediamine 65/35 are reacted in accordance with Example 1 with 4.1 g of an Al/Zn alloy consisting of 80% by weight of aluminum and 20% by weight of Zn and 8.3 g of aluminum chloride (anhydrous). The evolution of hydrogen is complete after 22 minutes.

The alkylation product, which was prepared analogously to Example 1, contains 97.3% of diethyltoluylenediamine.

EXAMPLE 4

If 250 g of toluylenediamine 65/35, 8.3 g of aluminum chloride (anhydrous) and 3.65 g of an Al/Zn alloy (90% by weight of Al/10% by weight of Zn) or 3.45 g of an Al/Zn alloy (95% by weight of Al/5% by weight of Zn) are employed, alkylation products having a 96.9% content of the two diethyltoluylenediamines are obtained in each case.

EXAMPLE 5

2,4-Toluylenediamine was reacted with ethylene analogously to Example 1. The alkylation product contains 96.9% of 1-methyl-3,5-diethyl-2,4-phenylenediamine. The reaction time is 45 minutes.

EXAMPLE 6

If 2,6-toluylenediamine is employed analogously to Example 5, an alkylation product containing 97.3% of 1-methyl-3,5-diethyl-2,6-phenylenediamine is obtained. The reaction time is 25 minutes.

EXAMPLE 7

A mixture consisting of 80% by weight of 2,4-toluylenediamine and 20% by weight of 2,6-toluylenediamine is reacted with ethylene analogously to Example 1. An alkylation product having a 95.5% content of the corresponding diethyltoluylenediamines is obtained.

What is claimed is:

1. A process for the ortho-alkylation of m-phenylenediamine or a m-phenylenediamine which contains one or more alkyl, cycloalkyl or aralkyl groups having 1 to 8 carbon atoms which comprises heating said m-phenylenediamine in the presence of an aluminum/zinc alloy, said aluminum/zinc alloy having a zinc content of 2 to 30% by weight and an aluminum content of 70 to 98% by weight, said aluminum/zinc alloy being employed in an amount of 0.5 to 4.0% by weight, based upon the weight of the m-phenylenediamine, and aluminum chloride, said aluminum chloride being employed in an amount of 1.0 to 7.0% by weight, based on the weight of the m-phenylenediamine, and contacting the so heated m-phenylenediamine with a lower alkene at a pressure of 50 to 250 bar and at a temperature of 250° to 330° C. when evolution of hydrogen from the heated m-phenylenediamine is complete.

2. A process according to claim 1 wherein the aluminum/zinc alloy has a zinc content of 5 to 20% by weight and an aluminum content of 80 to 95% by weight.

3. A process according to claim 1 wherein said m-phenylenediamine is selected from the group consisting of m-phenylenediamine, 2,4-toluylenediamine, 2,6-toluylenediamine, 1-ethyl-2,4-phenylenediamine, 1-ethyl-2,6-phenylenediamine, 1-propyl-2,4-phenylenediamine, 1,3-dimethyl-4,6-phenylenediamine and 1-benzyl-2,4-phenylenediamine.

4. A process according to claim 3 wherein the aluminum/zinc alloy has a zinc content of 2 to 30% and an aluminum content of 70 to 98% by weight, the aluminum/zinc alloy is employed in an amount of 0.5 to 4.0% by weight, based upon the weight of the m- phenylenediamine and the aluminum chloride is employed in an amount of 1.0 to 7.0% by weight, based upon the weight of the m-phenylenediamine.

5. A process according to claim 4 wherein the reaction with the alkene is carried out under a pressure of 50 to 250 bar at a temperature of 250° to 330° C.

6. A process according to claim 5 wherein the alkene is ethylene or propylene.

7. A process according to claim 1, wherein said m-phenylenediamine contains one or more alkyl, cycloalkyl or aralkyl groups having 1 to 3 carbon atoms.

8. A process according to claim 1, wherein said aluminum/zinc alloy is employed in an amount of 1 to 2% by weight, based upon the weight of the m-phenylenediamine.

9. A process according to claim 1, wherein the aluminum chloride is present in an amount of 2.5 to 4% by weight, based on the weight of the m-phenylenediamine.

10. A process according to claim 1, wherein the temperature of the heating of the m-phenylenediamine in the presence of the aluminum/zinc alloy and the aluminum chloride is 150° C. to 250° C.

11. A process according to claim 1, wherein the temperature of the heating of the m-phenylenediamine in the presence of the aluminum/zinc alloy and the aluminum chloride is 170° C. to 220° C.

12. A process according to claim 1, wherein the reaction of the alkene is carried out at a temperature of 280° C. to 310° C.

13. A process according to claim 1, wherein the reaction of the alkene is carried our under a pressure of 80 to 120 bar.

* * * * *